US00PP20238P2

(12) United States Plant Patent
Hooijman

(10) Patent No.: US PP20,238 P2
(45) Date of Patent: Sep. 1, 2009

(54) ***LIMONIUM* PLANT NAMED 'ESM JULIO'**

(50) Latin Name: *Limonium*
Varietal Denomination: Esm Julio

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 12/157,323

(22) Filed: Jun. 9, 2008

(51) Int. Cl.
*A01H 5/00* (2006.01)

(52) U.S. Cl. ..... Plt./449; Plt./358
(58) Field of Classification Search ..... Plt./449, Plt./358
See application file for complete search history.

(56) References Cited

PUBLICATIONS

UPOV–ROM citation European community PBR 2006138, published Aug. 15, 2006.*

* cited by examiner

*Primary Examiner*—Annette H Para
*Assistant Examiner*—Louanne C Krawczewicz Myers
(74) *Attorney, Agent, or Firm*—C. A. Whealy

(57) ABSTRACT

A new and distinct cultivar of *Limonium* plant named 'Esm Julio', characterized by its erect, long and strong flowering stems; vigorous growth habit; freely flowering habit; violet blue-colored flowers arranged on compact and dense panicles; and good postproduction longevity.

1 Drawing Sheet

Botanical designation: *Limonium sinuatum.*
Cultivar denomination: 'Esm Julio'.

BACKGROUND OF THE INVENTION

The present invention relates to a new and distinct cultivar of *Limonium* plant, botanically known as *Limonium sinuatum,* grown commercially as a cut flower, and hereinafter referred to by the name 'Esm Julio'.

The new *Limonium* is a product of a planned breeding program conducted by the Inventor in El Quinche, Pichincha, Ecuador. The objective of the breeding program is to create new vigorous and freely flowering *Limonium* cultivars with long and straight flowering stems.

The new *Limonium* originated from a open-pollination in El Quinche, Pichincha, Ecuador in July, 2001 of a proprietary selection of *Limonium sinuatum* identified as Line 130, not patented, as the female, or seed, parent with an unknown selection of *Limonium sinuatum.* The new *Limonium* was discovered and selected by the Inventor as a flowering plant from within the progeny of the stated open-pollination in a controlled greenhouse environment in El Quinche, Pichincha, Ecuador in January, 2003.

Asexual reproduction of the new *Limonium* by cuttings in a controlled greenhouse environment in El Quinche, Pichincha, Ecuador since February, 2003, has shown that the unique features of this new *Limonium* are stable and reproduced true to type in successive generations.

SUMMARY OF THE INVENTION

Plants of the new *Limonium* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Esm Julio'. These characteristics in combination distinguish 'Esm Julio' as a new and distinct cultivar of *Limonium:*

1. Erect, long and strong flowering stems.
2. Vigorous growth habit.
3. Freely flowering habit.
4. Violet blue-colored flowers arranged on compact and dense panicles.
5. Good postproduction longevity.

In side-by-side comparisons conducted in El Quinche, Pichincha, Ecuador, plants of the new *Limonium* differed from plants of the female parent selection in the following characteristics:

1. Plants of the new *Limonium* were larger and more vigorous than plants of the female parent selection.
2. Plants of the new *Limonium* produced more flowering stems than plants of the female parent selection.

Plants of the new *Limonium* can be compared to plants of the *Limonium sinuatum* 'Crystal Dark Blue', not patented. In side-by-side comparisons conducted in El Quinche, Pichincha, Ecuador, plants of the new *Limonium* differed from plants of 'Crystal Dark Blue' in the following characteristics:

1. Plants of the new *Limonium* were taller and narrower than plants of 'Crystal Dark Blue'.
2. Plants of the new *Limonium* were more vigorous than plants of 'Crystal Dark Blue'.
3. Plants of the new *Limonium* were more freely branching than plants of 'Crystal Dark Blue'.

4. Plants of the new *Limonium* had longer internodes than plants of 'Crystal Dark Blue'.
5. Plants of the new *Limonium* had stronger flowering stems than plants of 'Crystal Dark Blue'.
6. Plants of the new *Limonium* had smaller leaves than plants of 'Crystal Dark Blue'.
7. Plants of the new *Limonium* had slightly lighter colored sepals than plants of 'Crystal Dark Blue'.
8. Plants of the new *Limonium* had longer postproduction longevity than plants of 'Crystal Dark Blue'.

BRIEF DESCRIPTION OF THE PHOTOGRAPHS

The accompanying photographs illustrate the overall appearance of the new *Limonium*. These photographs show the colors as true as it is reasonably possible to obtain in colored reproductions of this type. Colors in the photographs may differ slightly from the color values cited in the detailed botanical description which accurately describe the colors of the new *Limonium*. Clockwise from the upper left photograph:

close-up view of a typical inflorescence of 'Esm Julio';

side perspective view of a typical flowering stem of 'Esm Julio';

and close-up view of upper and lower surfaces of typical leaves.

DETAILED BOTANICAL DESCRIPTION

Plants used for the aforementioned photographs and following observations and measurements were grown during the winter in El Quinche, Pichincha, Ecuador in ground beds in a polyethylene-covered greenhouse and under conditions and practices which approximate those generally used in commercial cut *Limonium* production. During the production of the plants, day temperatures ranged from 12° C. to 30° C. night temperatures ranged from 5° C. to 11° C. and light levels ranged from 1,000 to 1,200 foot-candles. Plants were pinched one time about nine weeks after planting. Plants were five months from planting when the photographs, observations and measurements were taken. In the following description, color references are made to The Royal Horticultural Society Colour Chart, 2001 Edition, except where general terms of ordinary dictionary significance are used.

Botanical classification: *Limonium sinuatum* 'Esm Julio'.
Commercial classification: Cut flower *Limonium*.
Parentage:
- *Female, or seed, parent.*—Proprietary selection of *Limonium sinuatum* identified as Line 130, not patented.
- *Male, or pollen, parent.*—Unknown selection of *Limonium sinuatum,* not patented.

Propagation:
- *Type.*—By cuttings.
- *Time to initiate roots.*—About seven to ten days at 26° C. to 30° C.
- *Time to produce a rooted cutting.*—About four to five weeks at 22° C. to 26° C.
- *Root description.*—Fine, fibrous; color, close to 200D.

Plant description:
- *Appearance.*—Perennial subshrub grown as a cut flower. Erect and strong flowering stems; inverted triangle form. Leaves basal. Freely flowering habit; numerous flowers arranged in symmetrical, compact and dense panicles. Vigorous growth habit.
- *Branching habit.*—Freely branching habit; after pinching, about 81 flowering stems develop per year.
- *Plant height.*—About 110 cm to 120 cm.
- *Plant diameter or spread.*—About 73 cm.
- *Flowering stems.*—Length: About 105 cm to 115 cm. Diameter: About 7 mm. Internode length: About 11 cm. Strength: Strong. Texture: Pubescent, rugose. Color: Close to 143A.

Foliage description:
- *Arrangement.*—Alternate, simple; sessile.
- *Length.*—About 24 cm.
- *Width.*—About 4.7 cm.
- *Shape.*—Narrowly obovate; deeply dissected, sinuate.
- *Apex.*—Acute.
- *Base.*—Attenuate.
- *Margin.*—Sinuate; ciliate.
- *Texture, upper and lower surfaces.*—Pubescent.
- *Venation pattern.*—Pinnate.
- *Color.*—Developing foliage, upper and lower surfaces: Close to 144A. Fully expanded foliage, upper surface: Close to 137A; venation, close to 194A. Fully expanded foliage, lower surface: Close to 137B; venation, close to 144A.

Flower description:
- *Flower arrangement and habit.*—Compact and dense panicles with numerous flowers; flowers actinomorphic and symmetrical. Freely flowering habit, about 550 flowers per inflorescence. Flowers face mostly upright.
- *Flowering response.*—In Ecuador, plants flower year round. Plants begin flowering about 17 to 18 weeks after planting.
- *Post-production longevity.*—As a cut flower, flowers last for about two weeks. Corolla not persistent; calyx persistent.
- *Fragrance.*—None detected.
- *Inflorescence height.*—About 105 cm to 115 cm.
- *Inflorescence diameter.*—About 22 cm.
- *Flower diameter.*—About 7 mm.
- *Flower depth (height).*—About 1.6 cm.
- *Flower buds.*—Length: About 7 mm. Diameter: About 1.7 mm. Shape: Ellipsoidal. Color: Towards the apex, close to N78C; mid-section, close to 149D; towards the base, close to 144C.
- *Corolla.*—Petals per flower: About five. Petal length: About 1.5 cm. Petal width: About 3.7 mm. Petal shape: Roughly deltoid. Petal apex: Emarginate to obtuse. Petal margin: Entire. Petal texture, upper and lower surfaces: Smooth, glabrous; membraneous. Petal color: When opening, upper and lower surfaces: Close to 145D; throat, close to 155D. Fully opened, upper and lower surfaces: Close to 149D; tube, close to 155D.
- *Calyx.*—Sepals per flower: Five. Length: About 1.6 cm. Diameter: About 8.6 mm. Shape: Salverform. Sepal apex: Acute. Sepal margin: Entire. Sepal texture, upper and lower surfaces: Smooth, glabrous. Sepal color: When opening, upper surface: Close to 90C; throat, close to 144D. When opening, lower surface: Close to N88B; tube, close to 145C. Fully opened, upper surface: Close to 90C; venation at base, close to 77C; throat, close to 144D. Fully opened, lower surface: Close to N88B; venation at base, close to 72D; tube, close to 145C.

*Pedicels.*—Length: About 47 cm. Diameter: About 7 mm. Strength: Strong. Angle: About 23° from vertical. Texture: Smooth, glabrous. Color: Close to 143A.

*Reproductive organs.*—Androecium: Stamen number: About five per flower. Anther shape: Rounded. Anther length: About 1.3 mm. Anther color: Close to 150C. Amount of pollen: Abundant. Pollen color: Close to 1C. Gynoecium: Pistil number: One per flower. Pistil length: About 1.1 cm. Style length: About 8 mm. Style color: Close to 155D. Stigma shape: Filiform. Stigma color: Close to 155D. Ovary color: Close to 145C.

Seeds/fruits. —Seed and fruit development have not been observed.

Disease/pest resistance: Plants of the new *Limonium* have not been observed to be resistant to pathogens and pests common to *Limonium.*

Temperature tolerance: Plants of the new *Limonium* have been observed to tolerate temperatures ranging from about 5° C. to about 30° C.

It is claimed:

1. A new and distinct *Limonium* plant named 'Esm Julio' as illustrated and described.

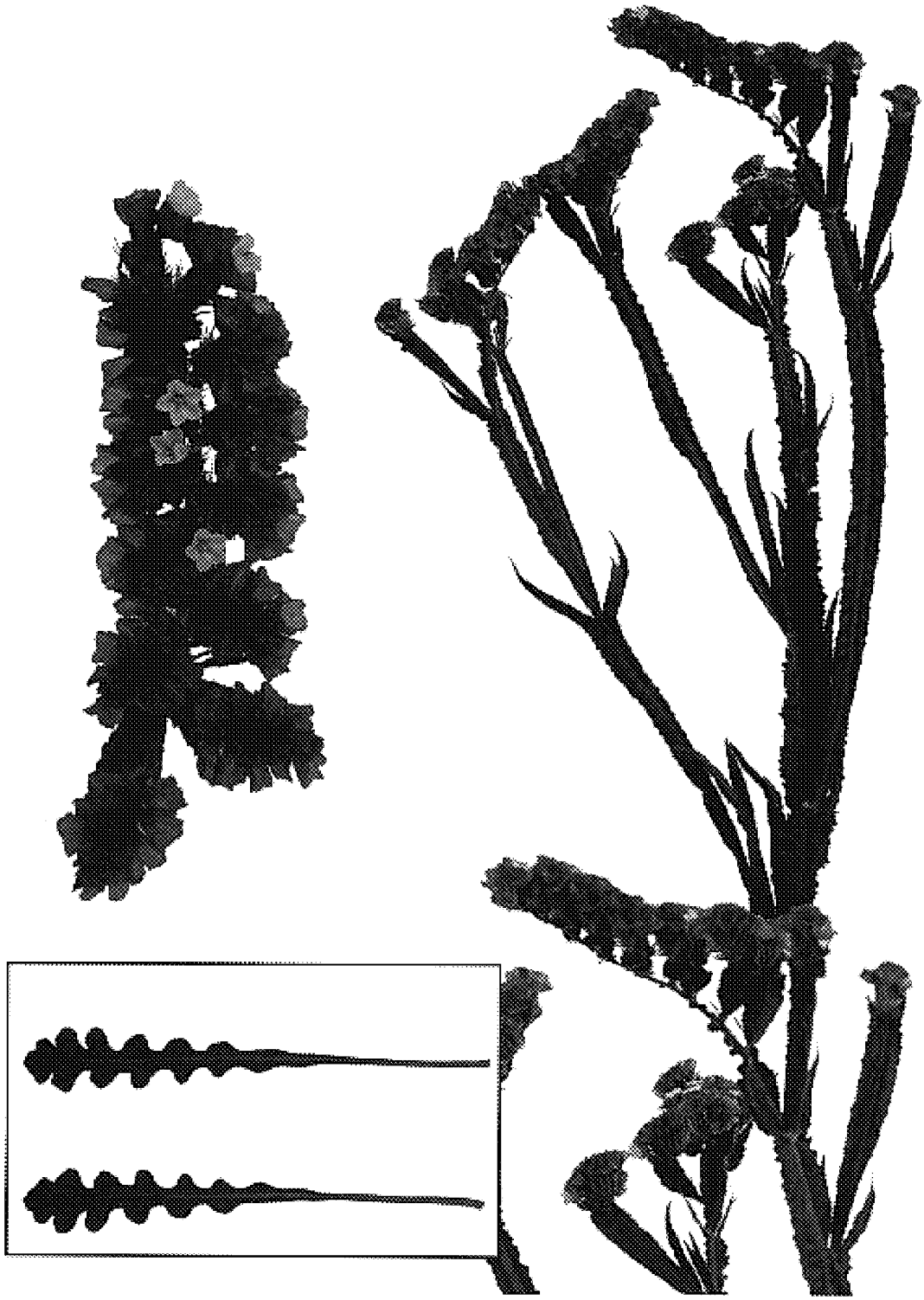

* * * * *